United States Patent [19]

Babb et al.

[11] Patent Number: 5,154,887

[45] Date of Patent: Oct. 13, 1992

[54] PHENALENIMINE FLUORESCENT DYES AND THEIR USE IN ANALYTICAL COMPOSITIONS, ELEMENTS AND METHODS

[75] Inventors: Bruce E. Babb; Fred T. Oakes, both of Rochester, N.Y.

[73] Assignee: Eastman Kodak Company, Rochester, N.Y.

[21] Appl. No.: 705,874

[22] Filed: May 28, 1991

[51] Int. Cl.$^5$ .............................................. C01N 33/53
[52] U.S. Cl. ...................................... 422/56; 435/7.5; 435/795; 435/805; 435/7.93; 435/7.94; 435/7.32; 435/7.31; 436/523; 436/533; 436/541; 436/546; 546/285; 546/75; 564/270; 252/586; 252/589; 252/301.16
[58] Field of Search .............. 436/501, 518, 523, 524, 436/525, 533, 541, 546, 810; 435/4, 2.1, 7.5, 2.63, 2.95, 805; 422/55, 56, 57, 58; 546/285, 75; 564/270; 252/582, 586, 588, 589, 301.16

[56] References Cited

U.S. PATENT DOCUMENTS 3,992,158 11/1976 Przybylowicz et al. .............. 422/58
4,857,271 8/1989 Belly et al. ............................ 422/55

OTHER PUBLICATIONS

STN-CAS Abstract Accession No.: CA 108(18):158857t—"Spectral characteristics of excitation states of phenalene amino derivative in Ethanol" Aladov, A. V.; Ryl'kov, V. V.; Reznichenko, A. V.; Kokin, V. N.; Opt. Spektrosk., 64(1) (1988) pp. 51-56, Resgistry No. 113702-10-0.

Franz et al, Tetrahedron, 34, pp. 2147-2151 (1978).

Solodar et al, Zh. Orgn. Khim., 16(5), pp. 1062-1064 (1980).

Primary Examiner—James C. Housel
Assistant Examiner—David Redding
Attorney, Agent, or Firm—J. Lanny Tucker

[57] ABSTRACT

Certain phenalenimine fluorescent compounds represented by the structure

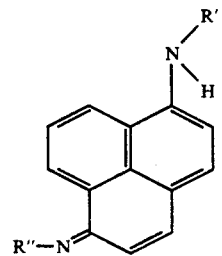

wherein R' and R" are independently hydrogen, alkyl, cycloalkyl, aryl or a heterocycle, or R' comprises the carbon and heteroatoms which form a fused ring with the compound nucleus, are useful in biomedical and analytical determinations. These compounds can be used for staining cells, as well as for the determination of various analytes found in human or animal biological fluids. Such determinations can be carried out in solution or by using dry analytical elements. The fluorescent compounds can be reacted with quinone nuclei to form reducible compounds which are also useful in analytical methods. In addition, the compounds can be incorporated into what are known as "loadable" latex particles to form detectable labels and biological reagents.

14 Claims, No Drawings

PHENALENIMINE FLUORESCENT DYES AND THEIR USE IN ANALYTICAL COMPOSITIONS, ELEMENTS AND METHODS

This is a division of application Ser. No. 215,478 filed Jul. 5, 1988 now U.S. Pat. No. 5,055,414.

FIELD OF THE INVENTION

This invention relates to a class of phenalenimine fluorescent compounds and reducible compounds. It also relates to analytical compositions, elements and methods utilizing such compounds. Moreover, it relates to fluorescent labels and fluorescent labeled biological reagents useful in biomedical studies and various analytical determinations.

BACKGROUND OF THE INVENTION

In the fields of medicine, biomedical research and diagnostic and clinical chemistry, there is often a need to visibly detect a cell or component thereof in order to effectively examine, diagnose or treat an animal or person. Many colorimetric and fluorometric compounds have been used for such detection. For example, copending and commonly assigned U.S. Ser. No. 824,757, filed Jan. 31, 1986, now U.S. Pat. No. 4,803,161 by Babb et al describes novel phenalenone and benzphenalenone fluorescent compounds and reducible precursors which are useful in various medical and diagnostic applications, such as for staining cells and for detecting microorganisms.

Many studies and determinations of physiologically reactive species (that is, species which will react in a specific binding reaction with a complementary binding partner, such as cell components, proteins, peptides, polypeptides, carbohydrates, nucleic acids, haptens and other materials known in the art) are carried out using "labels" which facilitate the detection or separation of the materials of interest at low concentrations. In one such application, the diagnosis of pathological conditions and the detection of drugs or narcotics is often carried out using labeled materials in specific binding assays using competitive binding principles.

Whenever labels are used, sensitivity is of prime importance due to the generally low levels of detectable species present. Radiometric labels have several drawbacks including limited sensitivity, short useful life and handling hazards. Various colorimetric labels can be incorporated into latex particles for use in analytical methods, but the dyes may be hard to detect and provide limited sensitivity.

Fluorescence spectroscopy, one of the most sensitive and versatile of the optical analytical techniques, has become increasingly popular in recent years to overcome the drawbacks of other labeling techniques. Fluorescent labels for immunoassays are described in U.S. Pat. Nos. 4,259,313 (issued Mar. 31, 1981 to Frank et al) and related 4,283,382 (issued Aug. 11, 1981 to Frank et al) which describe labeled polymeric particles useful in immunoassays.

After appropriate excitation, many known fluorescent compounds used in biological methods emit radiation at a wavelength less than 600 nm. In such cases, detection of the component of interest can be interfered with by other components commonly found in biological samples and which emit electromagnetic radiation at or near the emission wavelength of the fluorescent compound. To overcome this, various filtration steps can be carried out to remove interferents but this results in a tedious and costly procedure. It would be highly desirable to have fluorescent compounds which are detectable at a wavelength at or above about 600 nm. It would also be useful to have such compounds as labels in analytical procedures, and incorporated in precursors which are fluorescent only after appropriate chemical treatment.

SUMMARY OF THE INVENTION

Novel fluorescent compounds which are detectable at a wavelength at or above about 600 nm are those represented by the structure

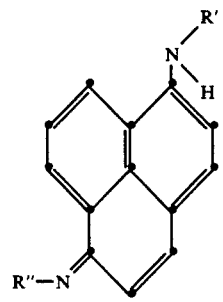

wherein R' and R" are independently hydrogen, alkyl, cycloalkyl, carbocyclic aryl or a heterocycle, or R' comprises the carbon or heteroatoms which form a fused ring with the compound nucleus. These compounds can be used in aqueous compositions buffered to a pH of 9 or less.

This invention also provides a fluorescent label comprising the fluorescent compound identified above which is incorporated into polymeric particles which are derived from a loadable latex having a discontinuous phase and an aqueous phase. This fluorescent label can be used to provide a fluorescent labeled biological reagent comprising a biological compound bound thereto.

A dry analytical element useful in analytical or diagnostic methods comprises an absorbent carrier material having one or more zones, and contains in at least one of the zones a fluorescent labeled biological reagent as described above.

Further, a method for the determination of a specific binding ligand in an aqueous liquid comprises the steps of:

A. in the presence of a receptor for the ligand, contacting a sample of the liquid with a fluorescent labeled specific binding ligand analog comprising a specific binding ligand bound to the fluorescent label described above, to form a complex between the receptor and the ligand analog, B. separating the complex from uncomplexed materials, and C. fluorimetrically detecting either the complex or the uncomplexed materials at a wavelength greater than or equal to about 600 nm.

In another method of this invention, a specific binding ligand is determined in an aqueous liquid by A. contacting a sample of the liquid with a fluorescent labeled specific binding reagent comprising a receptor for the ligand bound to a fluorescent label as described above, to form a complex between the receptor and the ligand, and B. fluorimetrically detecting the complex at a wavelength greater than or equal to 600 nm.

A method for staining a biological specimen comprises the steps of:

A. contacting a biological specimen with a composition buffered to a pH of from about 9 or less and comprising a fluorescent compound as identified above, and B. detecting stained material at a wavelength greater than or equal to about 600 nm.

This invention also provides a reducible precursor compound of the structure:

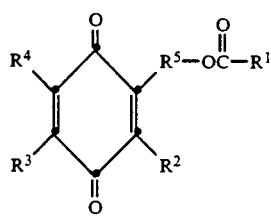

wherein $R^1$ is a monovalent fluorescent moiety derived from the fluorescent compound identified above, $R^2$ and $R^4$ are independently hydrogen, alkyl, aryl or an electron withdrawing group, $R^5$ is methylene, and $R^3$ is

or it is hydrogen, alkyl, aryl or an electron withdrawing group as defined for $R^2$ and $R^4$, or $R^3$ and $R^4$, taken together, represent the atoms necessary to complete a fused carbocyclic ring.

This reducible precursor compound can be included in at least one zone of a dry analytical element comprising an absorbent carrier material having one or more zones.

The reducible compound can be used in a method for the determination of an analyte comprising the steps of:

A. at a pH of 9 or less, contacting a sample of a liquid suspected of containing an analyte with a reducible compound, as identified above, to release a fluorescent dye, and B. determining the released fluorescent dye at a wavelength greater than or equal to about 600 nm as a result of the presence of the analyte.

The compounds of this invention can be used in rapid and highly sensitive assays even when the analytes are present in low concentrations. Spectral interferents are avoided because the compounds fluoresce at a wavelength at or above about 600 nm which is generally higher than most interferents found in biological specimens. The fluorescent compounds can be readily attached to quinone carriers to provide precursors which release dyes when the precursor is reduced in the presence of the analyte. In addition the fluorescent compounds can be used for staining biological specimens and can be "loaded" into loadable polymeric particles to form fluorescent labels and biological reagents.

DETAILED DESCRIPTION OF THE INVENTION

The fluorescent compounds of this invention are phenalenimine compounds represented by the structure

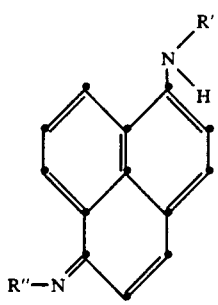

wherein R' and R" are independently (that is, the same or different) hydrogen, substituted or unsubstituted alkyl (generally of 1 to 20 carbon atoms, such as methyl, ethyl, isopropyl, hexyl, chloromethyl, methoxymethyl, methoxyethyl, benzyl, dodecyl and hexadecyl, and preferably of 1 to 10 carbon atoms), substituted or unsubstituted cycloalkyl (generally of 5 to 7 carbon atoms, such as cyclopentyl, cyclohexyl, 4-methylcyclohexyl, 2,3-dichlorocycloheptyl, and preferably of 5 or 6 carbon atoms), substituted or unsubstituted carbocyclic aryl (generally of 6 to 14 carbon atoms, such as phenyl, napthyl, tolyl, xylyl, 4-chlorophenyl, and preferably of 6 to 10 carbon atoms), or a substituted or unsubstituted heterocycle [aromatic or nonaromatic, generally of 5 to 7 carbon and hetero atoms (for example, nitrogen, sulfur and oxygen), such as pyridyl, pyrimidyl, imidazolyl, thienyl, pyrrolyl, furyl, and preferably of 5 or 6 carbon and hetero atoms]. Alternatively, R' comprises the carbon and hetero atoms (for example, oxygen, sulfur, nitrogen) necessary to form a fused ring with the compound nucleus (generally of 5 to 7 carbon and hetero atoms, which ring can be substituted with one or more alkyl, cycloalkyl, aryl or heterocyclic groups as defined above, alkoxy groups, such as methoxy, ethoxy, propoxy and the like or halo groups such as chloro, fluoro and bromo).

The compound of this invention can have one or more additional electron donating substituents on the phenalenimine nucleus. Such groups generally exhibit negative Hammett sigma values calculated according to standard procedures described, for example, in Steric Effects in Organic Chemistry, John Wiley & Sons, Inc. 1956, pp. 570-574 and Progress in Physical Organic Chemistry, Vol. 2, Interscience Publishers, 1964, pp. 333-339. Representative electron donating substituents include substituted or unsubstituted alkoxy (preferably of 1 to 10 carbon atoms), substituted or unsubstituted aralkoxy (preferably of 7 to 14 carbon atoms), primary, secondary and tertiary amines (including cyclic amines, such as amino, methylamino, dimethylamino, morpholino, piperidino and others known in the art), substituted or unsubstituted alkylazo, substituted or unsubstituted arylazo, substituted or unsubstituted alkyl carbonyloxy, substituted or unsubstituted arylcarbonyloxy, unsaturated alkyl, for example vinyl, allyl and alkynyl, and others known to those skilled in the art.

Preferred fluorescent compounds of this invention have the structure defined above wherein R' and R" are independently hydrogen, substituted or unsubstituted alkyl of 1 to 10 carbon atoms (methyl, ethyl and benzyl or substituted with chloro or alkoxy of the same number of carbon atoms) or substituted or unsubstituted aryl of 6 to 10 carbon atoms (phenyl, naphthyl, or aryl groups substituted with halo, alkyl or alkoxy groups as defined above). Particularly useful fluorescent compounds are selected from the group consisting of:

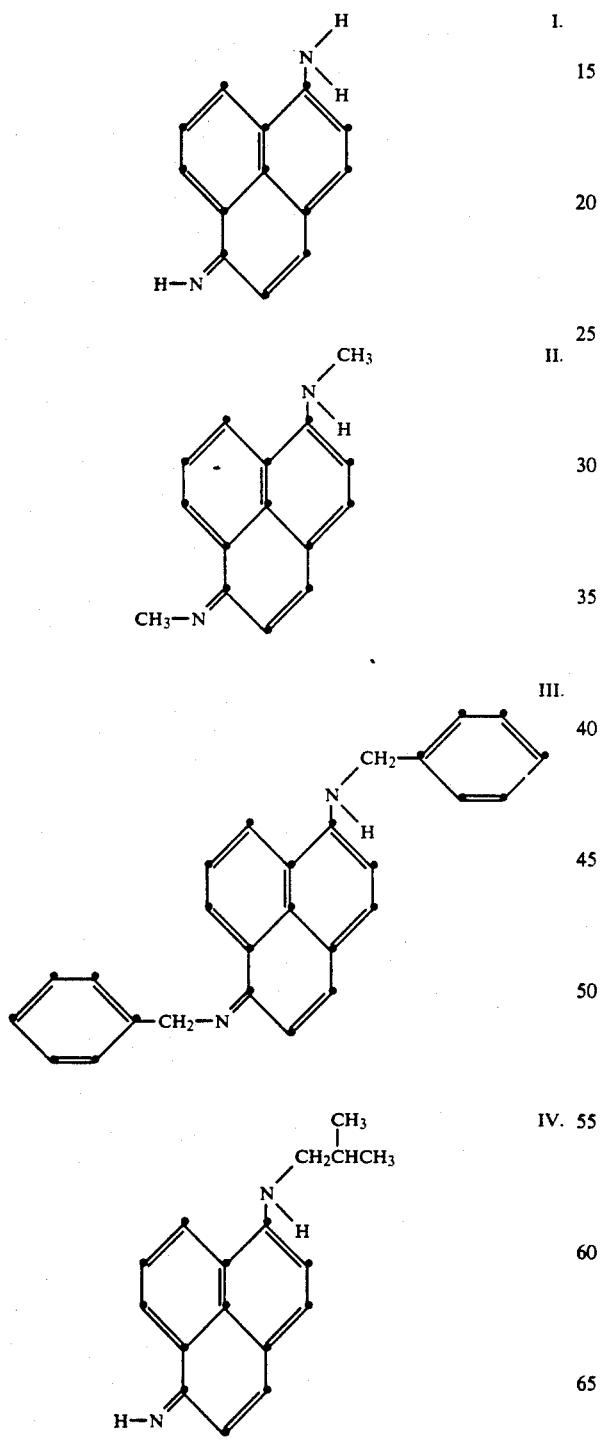

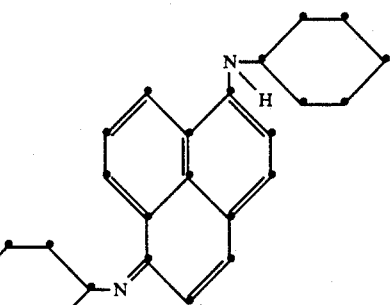

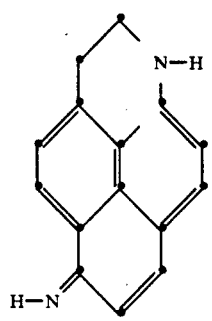

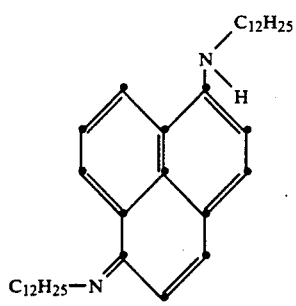

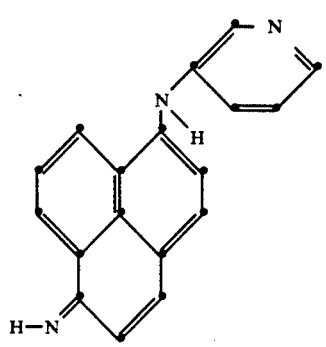

-continued

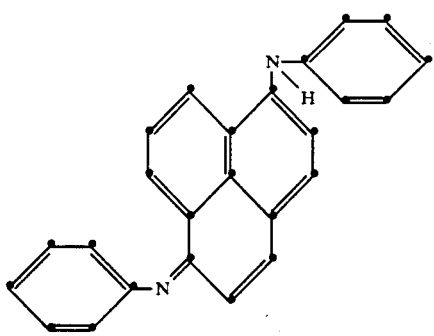

IX.

and

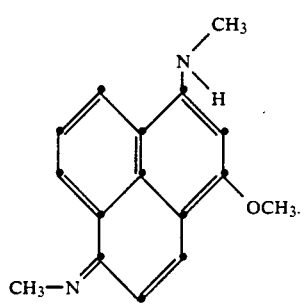

X.

Compounds I, II and III are most preferred in the practice of this invention.

The fluorescent compounds of this invention are prepared using the following general procedure (including general concentrations and temperature conditions) which is understandable to a skilled synthetic chemist. A 6-hydroxyphenalenone is converted to an alkyl ether (preferably the methyl ether) intermediate by the Williamson synthesis, that is, by alkylation of the phenoxide with an alkyl halide or alkyl sulfate. More specifically, the intermediate is produced by forming the alkoxide with a base, for example, potassium carbonate, treating with methyl iodide, heating for about 15 hours, cooling and isolating the 6-methoxyphenalenone intermediate. This intermediate is then condensed with an amine or ammonia (ammonium acetate) by heating at reflux in the presence of glacial acetic acid until all starting intermediate is converted to the imine product. Specific representative preparations are described in Examples 1, 2 and 3 below.

The fluorescent compounds of this invention can be kept and used in nonbuffered or buffered aqueous solutions. Preferably, they are kept and used in solutions buffered to a pH of 9 or less, and generally at a pH of 5 to 9 which is often considered physiological pH. Useful buffers are well known in the art and include phosphates, borates and organic buffers, some of which are described by Good et al, *Biochem.* 5, 467 (1966) and *Anal. Biochem.* 104, 300 (1980).

In one embodiment of this invention, the fluorescent compounds are useful for staining biological specimens, for example tissues and cells, and for cell cytometry using standard techniques. Staining, for example is generally accomplished by mixing a suspension of cells with a buffered solution of a fluorescent compound present in a concentration of at least about 1 mmolar. The dyed cells can then be detected and viewed at a wavelength of about 600 nm or greater after exposure to the appropriate electromagnetic excitation using suitable equipment.

In another embodiment, the fluorescent compounds of this invention can be attached to a quinone nucleus to form reducible dye precursors. The precursors can be subjected to suitable treatment or conditions which will reduce the precursor and release the fluorescent moiety to form a dye from the nucleus during an assay. While attached to the reducible compound, the fluorescent moiety generally has an emission spectrum different from the emission spectrum (600 nm or greater) of the released dye.

More particularly, the reducible precursors are represented by the structure:

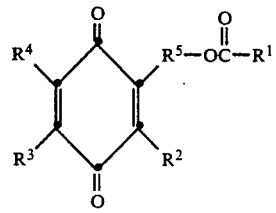

wherein $R^1$ is a fluorescent moiety derived from the fluorescent compound of this invention identified above. $R^1$ is attached to the

group through the amine group of the fluorescent compound upon the removal of a hydrogen atom, $R^2$ and $R^4$ are independently (that is, the same or different) hydrogen, substituted or unsubstituted alkyl, substituted or unsubstituted aryl or an electron withdrawing group, $R^5$ is substituted or unsubstituted methylene (such as substituted with an alkyl of 1 to 20 carbon atoms, and $R^3$ is

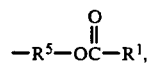

or it is hydrogen, substituted or unsubstituted alkyl, substituted or unsubstituted aryl or an electron withdrawing group as defined for $R^2$ and $R^4$ above, or $R^3$ and $R^4$, taken together, represent the atoms necessary to complete a substituted or unsubstituted fused carbocyclic ring.

Preferably, in the reducible compound structure shown above, $R^2$ and $R^4$ in the above quinone structure are independently hydrogen, substituted or unsubstituted alkyl of 1 to 40 carbon atoms (for example, methyl, ethyl, chloromethyl, hydroxymethyl, methoxymethyl, benzyl and others known to one skilled in the art) substituted or unsubstituted aryl (carbocyclic or heterocyclic, for example, phenyl, naphthyl, methylnaphthyl, p-nitrophenyl, m-methoxyphenyl, phenylsulfonamido, and others known to one skilled in the art) or an electron withdrawing group which generally has a positive Hammett sigma value, and preferably has a sigma value greater than about 0.06. Hammett sigma values are calculated in accordance with standard procedures described, for example, in the texts *Steric Effects* in *Organic Chemistry* and *Progress in Physical Organic Chemistry*, noted above. Representative electron withdrawing groups having positive Hammett sigma values include cyano, carboxy, nitro, halo (such as fluoro, bromo or chloro), trihalomethyl (for example, trifluoromethyl or trichloromethyl), trialkylammonium, carbonyl, carbamoyl, sulfonyl, sulfamoyl, esters and others known in the art. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can be

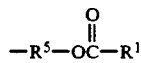

thereby potentially providing a 2:1 molar ratio of fluorescent moiety molecules to precursor molecules, or $R^3$ can be hydrogen, substituted or unsubstituted alkyl, substituted or unsubstituted aryl or an electron withdrawing group as defined above for $R^2$ and $R^4$.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone. The fused ring can be substituted with the groups defined for $R^2$ and $R^4$ above.

The reducible precursors of this invention can be prepared by treating the dye with phosgene in the presence of 2,6-lutidine to produce the chloroformamide from the amine group on the dye, and condensing the chloroformamide with a 2-hydroxymethylquinone to produce the reducible dye precursor. This procedure is illustrated in Example 4 below. Other details are provided in copending and commonly assigned U.S. Ser. No. 215,127 filed on even date herewith by Mooberry and entitled "Reducible Compounds Which Provide Aniline Dyes and Analytical Compositions, Elements and Methods Using Same", incorporated herein by reference.

The reducible precursor compounds just described can be used in aqueous solutions or dispersions for analytical purposes. If the precursors lack the needed water-solubility or -dispersibility, they can be solubilized using minor amounts of water-miscible organic solvents (for example, methanol, ethanol, propanol, N,N-dimethylformamide, dimethyl sulfoxide, acetonitrile, acetone or hexamethylenephosphoramide) or surfactants which do not inhibit reducibility of the precursor and release of the fluorescent dye. Useful surfactants include nonionic compounds which do not interfere with precursor reduction or with an assay, such as for microorganisms. The solutions or dispersions can be buffered to a pH of 9 or less if desired.

The reducible precursor compounds of this invention are useful in compositions for analytical determination (that is, qualitative, semiquantitative or quantitative detection) of chemical or biological materials in aqueous and nonaqueous liquids, for example, biological fluids, manufacturing effluents, wastewater, food stuffs, and other fluids. Determinations can be made of various analytes via a single reaction or a sequence of reactions which bring about reduction of the precursor and release of the fluorescent moiety. The various analytes include living cells (for example, bacteria, yeast, white blood cells or fungi), enzymes (for example, lipase, glucose oxidase, lactate oxidase, creatine kinase, α-glycerophosphate oxidase, lactate dehydrogenase, pyruvate dehydrogenase, glucose-6-phosphate dehydrogenase, alanine aminotransferase, aspartate aminotransferase and other NADH-based, FADH-based or oxidase-based assays which include dehydrogenase or reductase enzymes), biological or chemical reductants other than living cells (for example, ascorbates, cysteine, glutathione or thioredoxin), metabolizable substances (for example, glucose, lactic acid, triglycerides or cholesterol), immunoreactants (for example, antigens, antibodies or haptens).

The compositions can be used to monitor flavin-linked dehydrogenases and oxidases, including (NAD-NADH)-, (FAD-FADH)- and (NADP-NADPH)-based reactions. In such instances, the reducible precursor can be used to provide a fluorescent dye in place of NADH, FADH or NADPH.

When determining living cells using the reducible precursors, it is preferably for rapid dye release that the living cells interact with an electron transfer agent (herein ETA). The ETA is a mobile compound which acts as an intermediary between the substance being determined (for example, a living cell) and the reducible precursor.

In general, the ETA should be more easily reduced than the analyte and less easily reduced than the reducible precursor. They are generally present at a concentration that is dependant upon the concentration of the analyte, and preferably at a concentration of from about $1 \times 10^{-3}$ molar to about $1 \times 10^{-7}$ molar.

ETA compounds useful in the practice of this invention include phenazine methosulfate, phenazine ethosulfate, substituted benzo- and naphthoquinones such as those described in copending and commonly assigned U.S. Ser. No. 699,374 filed Feb. 7, 1985 by Mura et al, now U.S. Pat. No. 4,746,607 and similar compounds known to one skilled in the art. Combinations of different ETA compounds can be used if desired.

The determination of living cells, and particularly of bacterial cells, is often carried out in the presence of a metabolizable nutrient for those cells although its presence is not essential. Any nutrient medium can be used which contains useful carbon, and optionally nitrogen, sources. Suitable nutrient media having proper components and pH are well known in the art.

Use of the reducible precursors of this invention can be adapted to either solution or dry assays. In a solution assay, a solution (or aqueous dispersion) containing a reducible precursor, and preferably an ETA, can be prepared and contacted with a liquid test sample containing the living cells or analyte to be determined by mixing in a suitable container. The ETA can also be mixed with the test sample prior to mixing with the reducible precursor. The resulting solution (or dispersion) is gently mixed and incubated for a relatively short time (i.e. up to about 30 minutes) at a temperature up to about 40° C. The test sample is then evaluated by measuring the shift in fluorescence resulting from release of the fluorescent dye with suitable detection equipment.

The solution assay can also be carried out by contacting a porous, absorbent material, for example, a paper strip, containing the test sample with a dispersion of the reducible precursor. The analyte in the test sample can migrate from the porous material into the dispersion and initiate the analytical reactions needed for determination. In solution assays, the amount of precursor present is at least about 0.001 millimolar. Other reagents can be present in amounts readily determined by one skilled in the art.

Alternatively, the method of this invention can be practiced with a dry analytical element. Such an element can be an absorbent carrier material, i.e. a thin sheet or strip of self-supporting absorbent or bibulous material, such as filter paper or strips, which contains the precursor or a dried residue of the dispersion comprising same. Such elements are known in the art as test strips, diagnostic elements, dip sticks, diagnostic agents and the like.

When employed in dry analytical elements, the reducible precursors can be incorporated into a suitable absorbent carrier material by imbibition or impregnation, or can be coated on a suitable absorbent carrier material. Alternatively, they can be incorporated in the element during an assay. Useful carrier materials are insoluble and maintain their structural integrity when contacted with water or physiological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified by U.S. Pat. Nos. 3,092,465 (issued Jun. 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued Jun. 2, 1981 to Kondo et al), and U.K. Patent 2,052,057 (published Jan. 21, 1981).

A dry assay can be practiced to particular advantage with an analytical element comprising a support having thereon at least one porous spreading zone as the absorbent carrier material. The reducible precursor can be in the spreading or in other zones (for example, a reagent, registration or hydrophilic zone).

The spreading zone can be prepared using fibrous materials, either mixed with a suitable binder material or woven into a fabric, as described in U.S. Pat. Nos. 4,292,272 (issued Sep. 29, 1981 to Kitajima et al), polymeric compositions (for example, blush polymers) or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760 (published Jun. 24, 1982).

The dry analytical element of this invention can be a single self-supporting absorbent carrier material containing a reducible precursor and any other desired reagents for a particular use, but preferably such material is carried on a suitable nonporous support. Such a support can be any suitable dimensionally stable, and preferably, transparent (that is, radiation transmissive) film or sheet material which transmits electromagnetic radiation of a wavelength between about 200 and about 900 nm. Useful support materials include polystyrene, polyesters, polycarbonates and cellulose esters.

The elements can have a plurality of zones which are generally in fluid contact with each other, meaning that fluids, reagents and reaction products can pass between superposed regions of adjacent zones. Preferably, the zones are separately coated superposed layers, although two or more zones can be located in a single layer.

In the elements of this invention, the amount of the reducible precursor can be varied widely, but it is generally present in a coverage of at least about 0.01 $g/m^2$. Optional, but preferred reagents (for example, ETA, nutrient and buffer) are generally present in the following coverages:

| ETA: | generally at least about 0.001 $g/m^2$, |
|---|---|
| nutrient: | generally at least about 0.05 $g/m^2$ (used only in living cell detection), |
| buffer (pH $\leq$ 9): | generally at least about 0.1 $g/m^2$, and |
| surfactant: | generally at least about 0.1 $g/m^2$. |

In one embodiment of this invention, an element for detection of microorganisms (for example, yeast, fungi or bacteria) in an aqueous liquid comprises an electron transfer agent and a reducible precursor, both of which are described above. It is desirable that these elements also contain a nutrient for the living cells and a buffer which maintains suitable pH during the assay. Such an element can be used to detect bacteria, for example, in a urine sample by physically contacting the sample and element in a suitable manner, and detecting the fluorescent dye released from the precursor as a result of the presence of bacteria at the appropriate wavelength greater than or equal to about 600 nm.

In another of this invention, an element is used for the determination of a nonliving biological or chemical analyte in an aqueous liquid, and comprises an interactive composition which is capable of reacting with the reducible precursor to provide a fluorescent dye upon reduction. The amount of fluorescent dye detected can be correlated to the amount of analyte present in the liquid sample. A pretreatment step to remove interferences or to concentrate cells prior to assay may be desirable.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and contacting it with a sample (for example, 1–200 $\mu l$) of the liquid to be tested which mixes with the reagents in the element. Such contact can be accomplished in any suitable manner, for example, by dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

Detection of an analyte or living cell is achieved when the precursor is reduced releasing a fluorescent dye which can be detected in a suitable manner at a suitable wavelength at or above about 600 nm.

The fluorescent labels of this invention can also be used as probes, or labeling materials, for a variety of biomedical studies and clinical and diagnostic determinations. They can be used to label cells or other biological compounds including proteins, nucleic acids and nucleotides, enzymes, enzyme substrates, cofactors, viruses, leukocytes, growth factors, lectins, antigens, antibodies, haptens, vitamins, metabolites, hormones, toxins, radioisotopes, and others known to one skilled in the art. Many such biological compounds are specific binding ligands which will complex specifically with a corresponding receptor molecule. The labels are attached to such biological compounds in a suitable manner (as described below). Particularly useful biological compounds include avidin, biotin, enzymes and immunologically reactive compounds (such as antibodies and antigens).

The labels are particularly useful in specific binding assays to determine a species (that is, a specific binding ligand) which has specific binding capacity with a corresponding receptor molecule, for example an antigen to an antibody. In one embodiment, the species to be determined is attached to the label and the labeled species is placed in competition with unlabeled species from a test sample for reaction with the common receptor. The labels can also be used in what are known in the art as agglutination assays in which the presence of a species is detected using labeled, insolubilized receptor molecules which cause the species to clump together. The labels can be insoluble particles (labeled with the fluorescent compound of this invention) to which the receptor molecules are attached. Another embodiment is what is known as a sandwich or immunometric assay using two or more receptor molecules for the species to be detected. One of the receptors is attached to the fluorescent labels of the present invention.

In preferred embodiments of this invention, the specific binding ligand is an antigen or antibody and the specific binding assay is an immunoassay.

The fluorescent labels of this invention comprise latex polymer particles which contain the fluorescent compound of this invention. Useful polymeric particles are those which are "loadable", meaning that the fluorescent compound can be incorporated, or imbibed, into and distributed within preformed particles using the techniques described in more detail below.

Several techniques are known for distributing a hydrophobic compound, such as the fluorescent compound of this invention, in loadable polymeric latex particles. Such techniques are described, for example, in U.S. Pat. No. 4,199,363 (issued Apr. 22, 1980 to Chen) and 4,368,258 (issued Jan. 11, 1983 to Fujiwhara et al), and in copending and commonly assigned U.S. Ser. No. 136,214 filed Dec. 18, 1987 by Sutton, now abandoned. Generally "loading" the compound into the particles involves gradually using a water-miscible organic solvent containing dissolved fluorescent compound to carry the compound into particles which are partially softened in order to take up the compound in preference to the surrounding hydrophilic medium. The techniques noted in the art above involve various sequences of adding and mixing the various materials.

A preferred loading method is that described by the noted Sutton application in which a loadable latex (described below) is provided, a solution of fluorescent compound dissolved in one or more watermiscible organic solvents is provided, the loadable latex is heated to 30° to 95° C., and the organic solution is gradually added to the heated latex so that the polymeric particles and fluorescent compound are brought into intimate contact. The water-miscible solvent is diluted with water to reduce the solubility of the compound in the water, whereby the equilibrium distribution of the compound is driven away from the water towards the polymeric particles.

The proportion of loadable latex to fluorescent compound is generally maintained within the volume ratio of from about 30:1 to about 1:1. The weight ratio of fluorescent compound in the organic solution to polymeric particles is generally from about 1:30 to about 1:1.

Generally, loadable polymeric particles are those which meet the following test: at 25° C., the particles must (a) be capable of forming a latex with water at a particle concentration of from about 0.2 to about 20 percent, based on total latex weight, and (b) when a 100 ml sample of the latex is then mixed with an equal volume of the water-miscible organic solvent to be employed in forming the loaded latex composition, stirred and allowed to stand for 10 minutes, it exhibits no observable coagulation of polymeric particles.

The Sutton application noted above describes many polymers, details of preparing them and other features of loadable latices and conditions for loading them with fluorescent compounds which are useful in the practice of this invention.

Once a loaded latex has been prepared, a biological compound of interest (as described above) can be attached to particles by adsorption or by covalent attachment, assuming, of course, that the particles have surface reactive groups which are capable of reacting with the free amine or sulfhydryl groups of the biological compound. The particles or the biological compound can be chemically modified, if necessary, to facilitate attachment. Adsorption can be achieved using known techniques, usually mixing the particles and compounds for a suitable time at a suitable temperature. Covalent attachment techniques are more complex and preferred, but many such techniques are known in the art.

The resulting fluorescent biological reagents are useful in various analytical procedures as noted above, including competitive binding immunoassays, agglutination assays and immunometric assays. For instance, the reagents can be used as fluorescently labeled specific binding ligand analogs in immunoassays for a specific binding ligand. They can also be labeled reagents used in agglutination or immunometric assays having a receptor to the ligand of interest attached to insoluble particles.

These assays can be employed in solution, dry analytical elements (as described above) or test plates or devices as desired. Such articles are described in considerable technical and patent literature and are well within the skill of the ordinary worker in the art to design and use.

The following examples illustrate the practice of this invention.

EXAMPLE 1

Preparation of Fluorescent Compound I

Fluorescent compound I identified by structure above was prepared by the following procedure:

STEP 1

An intermediate, 6-hydroxyphenalenone (20 g), was dissolved in acetone (200 ml). This intermediate is prepared according to the procedure described by Cooke et al, *Austral. J. Chem.*, 11, pp. 230–235 (1958), specifically preparation (a) therein, or by Solodar et al, *Zhurnal Organicheskoi Khimii*, 16(5), pp. 1062-1064 (1980). A mixture of potassium carbonate (20 g), iodomethane (10 ml) and water (1 ml) was added to the acetone solution, and the resulting solution was heated under reflux for about 15 hours. After cooling, water was added, and the precipitated yellow product was collected by filtration.

The product was dissolved in alcohol, filtered, and the filtrate was diluted with water and chilled. The resulting crystalline solid was collected by filtration, washed with water, and dried at 25° C. under nitrogen. About 6 g of the product, 6-methoxyphenalenone, were obtained. Infrared and nuclear magnetic resonance spectroscopy confirmed the structure.

STEP 2

6-Methoxyphenalenone (6.3 g) and ammonium acetate (60 g) in glacial acetic acid (150 ml) were heated under reflux until starting material was no longer present, as determined by thin-layer chromatography (silica, 3:2 methanol, ethyl acetate). A reaction time of about one hour was required. The mixture was diluted to 500 ml with hot water, and the solution was filtered. The filtrate was treated with saturated sodium chloride solution and chilled in a methanol/ice bath. The precipitated dye was collected, then triturated with acetone to remove the 6-aminophenalenone by-product. The remaining solid was recrystallized from methanol to give 5 g of the desired compound I. Mass spectral analysis, nuclear magnetic resonance and infrared spectroscopy confirmed the structure. Compound I exhibited a maximum fluorescent emission at a wavelength of about 623 nm when excited at 573 nm in methanol with a fluorescence efficiency of 0.13.

EXAMPLE 2

Preparation of Fluorescent Compound II

Fluorescent compound II illustrated by structure above was prepared as follows:

A sample of 6-methoxyphenalenone (5 g) prepared as described in Example 1 was heated in an open vessel in glacial acetic acid (50 ml) and methylamine (30 ml). Water and glacial acetic acid were boiled off until the temperature reached 150° C. After the beaker was covered, heating was continued for about 3 hours at 170° C. After cooling, water was added to precipitate the crude product which was then dissolved in hot water containing a small amount of glacial acetic acid. The resulting solution was filtered, and the filtrate was treated with salt solution to precipitate the product which was collected and slurried in ethyl acetate. The solid was collected and recrystallized from methanol to obtain 2.1 g of compound II. Infrared and nuclear magnetic resonance spectroscopy confirmed the structure. Compound II exhibited a maximum fluorescent emission at a wavelength of about 615 nm when excited at 596 nm in ethanol with a fluorescence efficiency of 0.46.

EXAMPLE 3

Preparation of Fluorescent Compound III

Fluorescent compound III illustrated by structure above was prepared in the following manner:

A sample of 6-methoxyphenalenone (2.1 g), glacial acetic acid (10 ml) and benzylamine (10 g) were mixed in a flask and heated on a steam bath for 24 hours. Thin-layer chromatography (silica, 3:2 methanol, ethyl acetate) showed no starting material.

The reaction mixture was treated with dilute ammonium hydroxide and extracted with toluene. The toluene solution was washed three times with dilute saline solution, dried and concentrated. The resulting oil was dissolved in methanol, and 20% (v/v) water was added, and the solution was then chilled. The product was precipitated as a waxy solid (2 g). The material was recrystallized from methanol to give 0.5 g of compound III. Infrared, nucelar magnetic resonance and mass spectral analysis confirmed the structure of the compound. Compound III exhibited a maximum fluorescent emission wavelength of about 634 nm when excited at 589 nm in a pH 7.5 phosphate buffered solution with a fluorescence efficiency of 0.42.

EXAMPLE 4

Preparation of Reducible Compound 6-[N-(5,7-Ethano-5,6,7,8-tetrahydro-2-naphthoquinonylmethoxycarbonyl)-N-methylamino]-N'-methyl-1-phenalenimine A reducible compound of this invention was prepared by attaching fluorescent compound II to a quinone carrier moiety in the following manner:

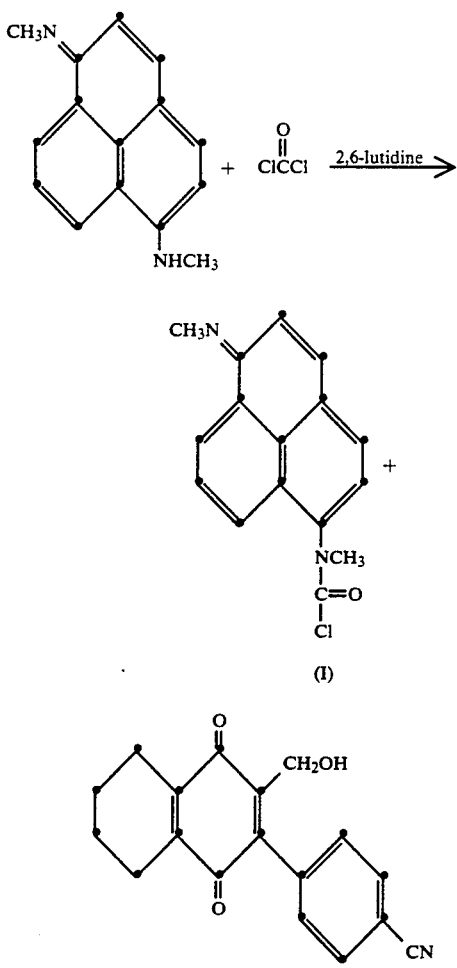

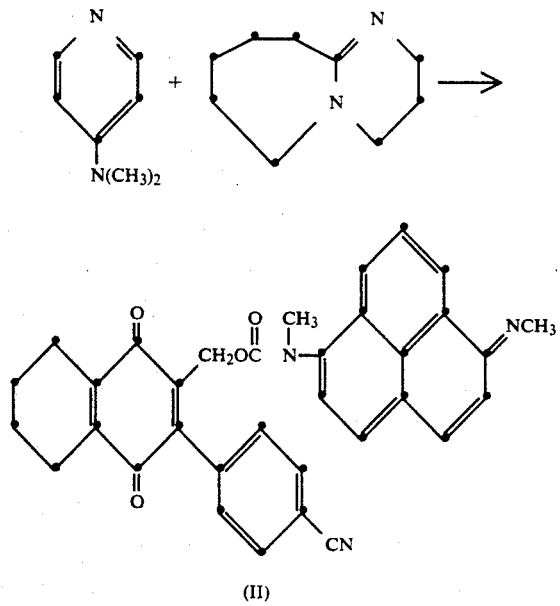

(II)

A mixture of 6-methylamino-N-methyl-1 phenalenimine (2.2 g) and 2,6-lutidine (5 ml) in dry acetonitrile (200 ml) was cooled to 0° C. A solution of 1 molar phosgene in toluene (15 ml) was added rapidly and stirred under nitrogen for 60 minutes while allowing the mixture to warm to room temperature. The mixture was washed with cold water to remove excess phosgene and the lutidine hydrochloride salt, and dried over magnesium sulfate.

3-(4-Cyanophenyl)-2-hydroxymethyl-5,6,7,8-tetrahydro-5,8-ethanonaphthoquinone (3.2 g) and 4-dimethylaminopyridine (0.13 g) were added to the dried solution. The resulting mixture was cooled to 0° C., treated with 2,3,4,6,7,8,9,10-octahydropyrimido-[1,2-a]-azepine (1.6 g), and stirred for 25 minutes at 0° C. A small amount of acetic acid was then added, the salts were washed out with ice cold water, the solution dried over magnesium sulfate, and the solvent removed on a rotary evaporator. The crude reducible compound was recrystallized from acetonitrile to yield about 1 gram.

EXAMPLE 5

Preparation of a Fluorescent Label By Loading Dye Compound III into Loadable Polymeric Latex Particles A latex of poly(styrene-co-vinylbenzylchloride-co-methacrylic acid) (molar ratio 50/30/20) was prepared containing about 17.23% solids. A dye solution of 0.12 g of fluorescent Dye III in 5 g of methanol was prepared and added to 6 g of the above latex (diluted with 92 g of water). The mixture was stirred for 15 minutes, then the methanol was removed under vacuum at 60° C. to produce a 1% dye/polymer stable loaded latex dispersion.

The invention has been described in detail with particular reference to preferred embodiments thereof, but it will be understood that variations and modifications can be effected within the spirit and scope of the invention.

I claim:

1. A fluorescent compound represented by the structure

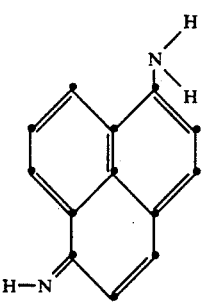

wherein R' and R" are independently hydrogen, alkyl, cycloalkyl, aryl or a heterocycle, or R' comprises the carbon or heteroatoms which form a fused ring with the compound nucleus.

2. The compound of claim 1 wherein R' and R" are independently hydrogen, alkyl of 1 to 10 carbon atoms or aryl of 6 to 10 carbon atoms.

3. The compound of claim 1 selected from the group consisting of:

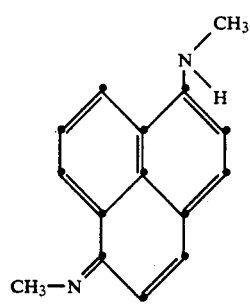

I.

II.

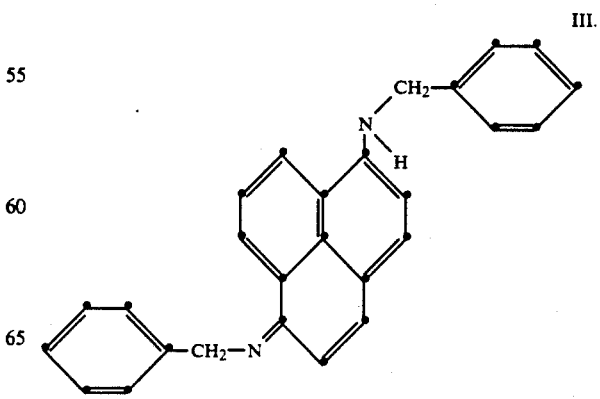

III.

-continued

IV. 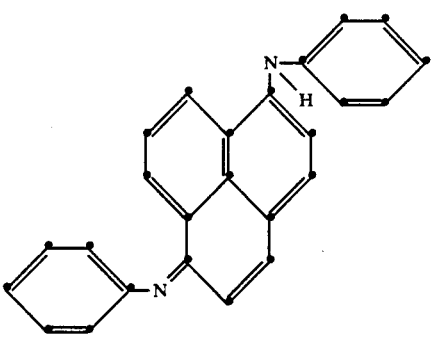

V. 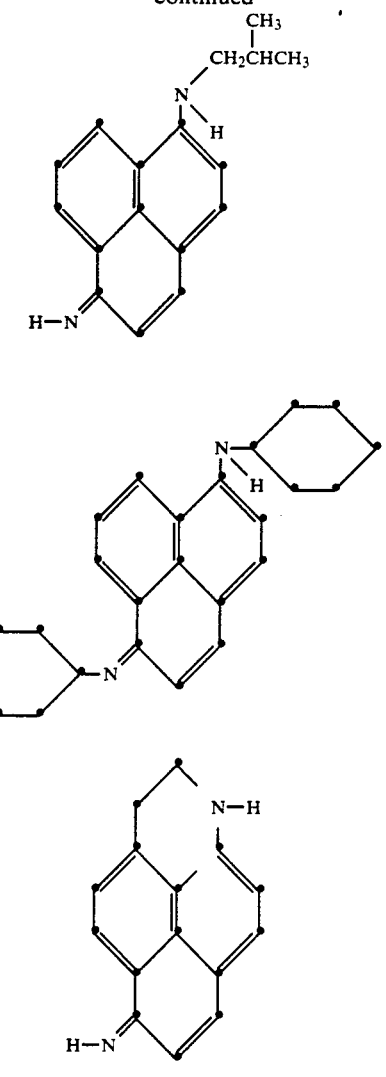

VI.

VII.

VIII. 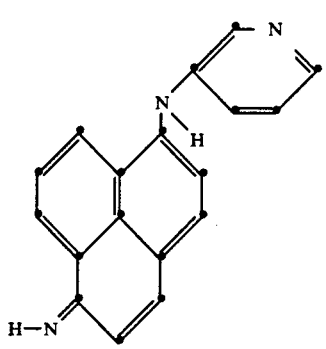

-continued

IX. 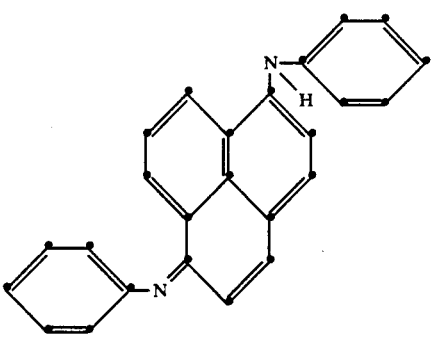

and

X. 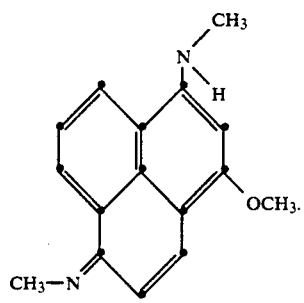

4. The compound of claim 3 which is Compound I, II or III.

5. A fluorescent label comprising a fluorescent compound incorporated into polymeric particles which are derived from a loadable latex having a discontinuous phase and an aqueous phase, said compound represented by the structure

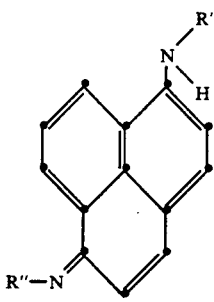

wherein R' and R" are independently hydrogen, alkyl, cycloalkyl, aryl or a heterocycle, or R' comprises the carbon or heteroatoms which form a fused ring with the compound nucleus.

6. A fluorescent labeled biological reagent comprising a biological compound bound to a fluorescent label comprising a fluorescent compound incorporated into polymeric particles which are derived from a loadable latex having a discontinuous phase and an aqueous phase, said compound represented by the structure

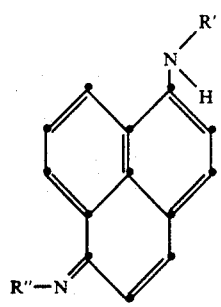

wherein R' and R" are independently hydrogen, alkyl, cycloalkyl, aryl or a heterocycle, or R' comprises the carbon or heteroatoms which form a fused ring with the compound nucleus.

7. The reagent of claim 6 wherein said biological compound is selected from the group consisting of avidin, biotin, enzymes and immunologically reactive compounds.

8. The reagent of claim 7 wherein said biological compound is an antibody.

9. The reagent of claim 6 wherein said biological compound is covalently attached to said fluorescent label.

10. A dry analytical element useful in analytical or diagnostic methods comprising an absorbent carrier material having one or more zones, and containing in at least one of said zones a fluorescent labeled biological reagent comprising a biological compound bound to a fluorescent label comprising a fluorescent compound incorporated into polymeric particles which are derived from a loadable latex having a discontinuous phase and an aqueous phase, said fluorescent compound represented by the structure

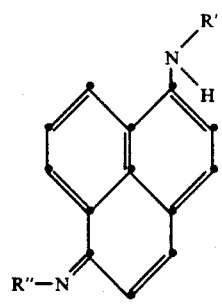

wherein R' and R" are independently hydrogen, alkyl, cycloalkyl, aryl or a heterocycle, or R' comprises the carbon or heteroatoms which form a fused ring with the compound nucleus.

11. An aqueous composition buffered to a pH less than about 9 and comprising a fluorescent compound represented by the structure

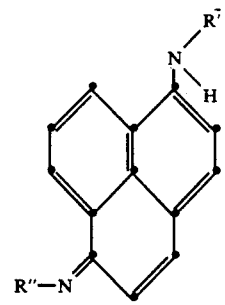

wherein R' and R" are independently hydrogen, alkyl, cycloalkyl, aryl or a heterocycle, or R' comprises the carbon or heteroatoms which form a fused ring with the compound nucleus.

12. A reducible precursor compound of the structure:

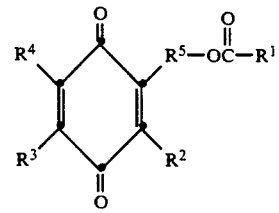

wherein $R^1$ is a monovalent fluorescent moiety derived from a fluorescent compound represented by the structure

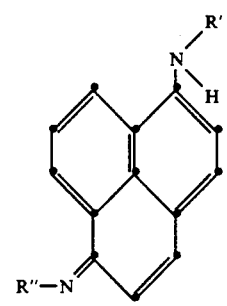

wherein R' and R" are independently hydrogen, alkyl, cycloalkyl, aryl or a heterocycle, or R' comprises the carbon or heteroatoms which form a fused ring with the compound nucleus, $R^2$ and $R^4$ are independently hydrogen, substituted or unsubstituted alkyl, substituted or unsubstituted aryl or an electron withdrawing group, $R^5$ is substituted or unsubstituted methylene, and $R^3$ is

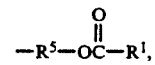

or it is hydrogen, substituted or unsubstituted alkyl, substituted or unsubstituted aryl or an electron withdrawing group, or $R^3$ and $R^4$, taken together, represent the atoms necessary to complete a substituted or unsubstituted fused carbocyclic ring.

13. A dry analytical element for the determination of an analyte comprising an absorbent carrier material having one or more zones, and in at least one of said zones a reducible precursor compound of the structure:

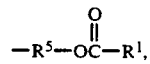

wherein $R^1$ is a monovalent fluorescent moiety derived from a fluorescent compound represented by the structure

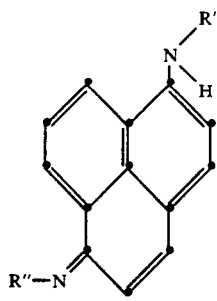

wherein R' and R" are independently hydrogen, alkyl, cycloalkyl, aryl or a heterocycle, or R' comprises the carbon or heteroatoms which form a fused ring with the compound nucleus, $R^2$ and $R^4$ are independently hydrogen, substituted or unsubstituted alkyl, substituted or unsubstituted aryl or an electron withdrawing group, $R^5$ is substituted or unsubstituted methylene, and $R^3$ is $$-R^5-O\overset{O}{\underset{\|}{C}}-R^1,$$

or it is hydrogen, substituted or unsubstituted alkyl, substituted or unsubstituted aryl or an electron withdrawing group, or $R^3$ and $R^4$, taken together, represent the atoms necessary to complete a substituted or unsubstituted fused carbocyclic ring.

14. The element of claim 13 further comprising an electron transfer agent.

* * * * *